United States Patent
Sandell

(10) Patent No.: US 7,560,273 B2
(45) Date of Patent: Jul. 14, 2009

(54) SLIP COVER FOR HEATED PLATEN ASSEMBLY

(75) Inventor: Donald R. Sandell, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 268 days.

(21) Appl. No.: 10/200,581

(22) Filed: Jul. 23, 2002

(65) Prior Publication Data

US 2004/0018610 A1 Jan. 29, 2004

(51) Int. Cl.
*C12M 1/34* (2006.01)
*C12M 1/38* (2006.01)

(52) U.S. Cl. .............. 435/288.7; 435/287.2; 435/303.1; 435/809; 422/943

(58) Field of Classification Search .............. 435/288.4, 435/288.7, 287.2, 292.1, 303.1, 305.3, 305.4, 435/808; 422/102; 356/246; 359/398; 219/428; 250/328

See application file for complete search history.

(56) References Cited

U.S. PATENT DOCUMENTS

| | | | | |
|---|---|---|---|---|
| 4,038,030 A | * | 7/1977 | Albright et al. ............. 436/165 |
| 4,039,247 A | * | 8/1977 | Lawman et al. ............. 359/398 |
| 4,652,127 A | | 3/1987 | Ekholm et al. |
| 5,282,543 A | | 2/1994 | Picozza et al. ............. 220/255 |
| 5,307,144 A | | 4/1994 | Hiroshi et al. .............. 356/244 |
| 5,320,808 A | | 6/1994 | Holen et al. ................. 422/64 |
| 5,342,581 A | | 8/1994 | Sanadi ....................... 422/101 |
| 5,346,672 A | | 9/1994 | Stapleton et al. ............. 422/102 |
| 5,364,790 A | | 11/1994 | Atwood et al. .............. 435/288 |
| 5,475,610 A | | 12/1995 | Atwood et al. .............. 364/500 |
| 5,496,517 A | | 3/1996 | Pfost et al. |
| 5,516,490 A | | 5/1996 | Sanadi |
| 5,567,617 A | | 10/1996 | Caprio et al. ............. 435/287.2 |
| 5,602,756 A | | 2/1997 | Atwood et al. .............. 364/500 |
| 5,604,130 A | | 2/1997 | Warner et al. ............. 435/286.7 |
| 5,661,028 A | | 8/1997 | Foote ....................... 435/287.2 |
| 5,710,381 A | | 1/1998 | Atwood et al. ........... 73/864.91 |
| 5,721,136 A | | 2/1998 | Finney et al. |
| 5,741,463 A | | 4/1998 | Sanadi |
| 5,851,492 A | | 12/1998 | Blattner ..................... 422/102 |
| 5,928,907 A | | 7/1999 | Woudenberg et al. ...... 435/91.2 |
| 6,015,674 A | | 1/2000 | Woudenberg et al. ......... 435/6 |
| 6,106,784 A | | 8/2000 | Lund et al. .................. 422/104 |

(Continued)

FOREIGN PATENT DOCUMENTS

DE 198 52 946 A1 5/2000

(Continued)

OTHER PUBLICATIONS

Sasaki et al. "A Novel Control System for Polymerase Chain Reaction Using a RIKEN GS384 Thermalcycler." DNA Research. vol. 4 (1997), pp. 387-391.*

(Continued)

*Primary Examiner*—William H Beisner

(57) ABSTRACT

A heated platen assembly for use in a biological testing device is disclosed having a heated platen defining a plurality of optical openings configured to permit radiation to pass through the heated platen, a light transmissive slip cover configured to cover at least one of the plurality of optical openings, and means for retaining the slip cover over the at least one of the plurality of optical openings.

14 Claims, 8 Drawing Sheets

U.S. PATENT DOCUMENTS

| | | | |
|---|---|---|---|
| 6,218,191 B1 | 4/2001 | Palander | 436/63 |
| 6,248,521 B1 | 6/2001 | Van Ness et al. | 435/6 |
| 6,254,833 B1 | 7/2001 | Shumate et al. | 422/102 |
| 6,258,325 B1 | 7/2001 | Sanadi | |
| 6,258,593 B1 | 7/2001 | Schembri et al. | 435/287.2 |
| 6,337,435 B1 * | 1/2002 | Chu et al. | 136/242 |
| 6,514,750 B2 | 2/2003 | Bordenkircher et al. | 435/286.2 |

FOREIGN PATENT DOCUMENTS

| | | |
|---|---|---|
| EP | 0 438 883 A2 | 7/1991 |
| EP | 0 488 769 A2 | 6/1992 |
| EP | 0 758 756 A1 | 2/1997 |
| WO | WO 89/12502 A1 | 12/1989 |
| WO | WO 95/30139 A1 | 11/1995 |
| WO | 97/21089 | 6/1997 |
| WO | WO 97/36681 | 10/1997 |
| WO | 98/07026 | 2/1998 |
| WO | WO 99/60381 A1 | 11/1999 |
| WO | WO 00/25922 | 5/2000 |
| WO | 01/08800 | 2/2001 |
| WO | WO 01/28684 A2 | 4/2001 |
| WO | WO 02/41999 A1 | 5/2002 |
| WO | 03/004166 | 1/2003 |

OTHER PUBLICATIONS

U.S. Appl. No. 09/977,225, filed Oct. 16, 2001, Freudenthal et al.
International Search Report for International application No. PCT/US03/22903 dated Oct. 24, 2003.
Response to grounds of opposition filed Jun. 13, 2007 with the European Patent Office. Opposition to European Patent No. 1 539 353.
Notice of Opposition against European Patent No. 1 539 353 dated Nov. 8, 2006.
Interlocutory Decision. Dated Feb. 15, 2008. Opposition to European Patent No. 1 539 353.
Submission of Corrected Auxiliary Request claims by Assignee. Dated Feb. 20, 2008. Opposition to European Patent No. 1 539 353.
Second Brief Submission by Opponent. Dated Dec. 21, 2007. Opposition to European Patent No. 1 539 353.
The Concise Oxford Dictionary, Oxford University Press, 1999, pages containing definition of "slip cover".
Gerhard Pahl, Wolfgang Beitz, "Kostruktionslehre", Springer, 4, Aufl. 1997, pp. 513-551. (German Language).
Submission of Proposed Auxiliary Request claims by Assignee. Dated Dec. 21, 2007. Opposition to European Patent No. 1 539 353.
Submission of Auxiliary Request claims, amended specification, and Affidavit by Douglas Grunewald by Assignee. Dated Jan. 21, 2008. Opposition to European Patent No. 1 539 353.
Dusseldorf Regional Court Decision. Dated Mar. 18, 2008. German Litigation of European Patent No. 1 539 353. (German Language).
Dusseldorf Regional Court Decision. Dated Mar. 18, 2008. German Litigation of European Patent No. 1 539 353. (English Translation).
Appeal Brief for Case No. T0439/08-3.305 in EPO Opposition against European Patent No. 1 539 353, Filed by Applera Corporation, Jun. 25, 2008.
Appeal Brief for Case No. T0439/08-3.305 in EPO Opposition against European Patent No. 1 539 353, Filed by Eppendorf AG, Jun. 25, 2008.
Appeal Brief for Case No. I-2 U 30/08 in Higher Regional Court Duesseldorf, Filed by Eppendorf AG, Aug. 4, 2008.
Translation of Appeal Brief for case No. I-2 U 30/08 in Higher Regional Court Duesseldorf, filed by Eppendorf AG, Aug. 4, 2008.
Feb. 5, 2008 Official Action of Japanese Application No. 2004-523290 and English translation.
Jun. 18, 2008 Final Official Action of Japanese Application Nos. 2004-523290 and English translation.
Jun. 18, 2008 Official Action of Japanese Application Nos. 2008-068435 and English translation.
Oct. 7, 2008 Official Action of Japanese Application No. 2008-068435 and English translation.
Oct. 1, 2008 Official Action of Japanese Application No. 2008-224158 and English translation.
Minutes of the Oral Proceedings of Feb. 17, 2009 for Appeal No. T0439/08-3.3.05. Patent No. 1 539 353 in the name of Applied Biosystems, Inc. dated Feb. 24, 2009.
Decision of the Technical Board of Appeal 3.3.05 of Feb. 17, 2009 for Appeal case No. T0439/08 - 3.3.05 dated Mar. 3, 2009.

* cited by examiner

SLIP COVER FOR HEATED PLATEN ASSEMBLY

FIELD

The present teachings relate to a heated platen assembly for use in biological testing devices. More particularly the present teachings relate to a light transmissive slip cover for covering at least one optical opening in such a heated platen assembly.

BACKGROUND

Biological testing has become an important tool in detecting and monitoring diseases. In the biological field, thermal cycling is utilized in order to perform polymerase chain reactions (PCR) and other reactions. To amplify DNA (deoxyribonucleic acid) using the PCR process, a specifically constituted liquid reaction mixture is cycled through a PCR protocol including several different temperature incubation periods. An aspect of the PCR process is the concept of thermal cycling: alternating steps of melting DNA, annealing short primers to the resulting single strands, and extending those primers to make new copies of double-stranded DNA. During thermal cycling, it may be desirable that the temperature of each of a plurality of sample wells is substantially uniform. In addition, it may be desirable that condensation be avoided on the caps or other covering for the sample wells.

One method of inhibiting condensation on the top of the sample wells is to provide a heated platen for pressing down on the tops or caps of the sample well trays. Such a pressing force is often accomplished by using one or more springs located around a periphery of the platen. The platen may typically be included as part of a cover and may typically be metal. The platen may transfer heat to the caps of the sample wells by utilizing a resistive element connected to the platen, thereby inhibiting condensation. In addition, the platen may press down on the sample well(s) so that the sample well outer conical surfaces are pressed firmly against the mating surfaces on the sample block. This may increase heat transfer to the sample well(s) and facilitate a uniform distribution of sample well temperatures. The platen may also prevent thermal leakage from the interior of the device. Examples of a system with a heated platen are described in U.S. Pat. Nos. 5,475,610, 5,602,756, and 5,710,381, all of which are assigned to the assignee of the present invention, and the contents of which are all hereby incorporated by reference herein.

It may also be desirable for the heated platen to allow optical access to the sample wells. To achieve this, the heated platen may have a plurality of optical openings passing through the heated platen to allow light to pass from a light source to the samples and then to a detection device. These holes, while providing the benefit of allowing optical access, also may facilitate heat loss through the holes and/or radiated from the upper surface of the platen. In addition to heat loss, as the thermal cycling device is used over time, dust or other foreign particles may accumulate in the optical openings, thus reducing the amount of light that may transmit through the heated platen.

SUMMARY

In one aspect, the present teachings include a heated platen defining a plurality of optical openings. The optical openings may be configured to permit radiation to pass through the heated platen and the heated platen may have a first side configured to face away from a plurality of sample wells and a second side configured to face toward the plurality of sample wells. The heated platen may also include a light transmissive slip cover configured to cover at least one of the plurality of optical openings on the first side of the heated platen. Means for retaining the slip cover over the at least one of the plurality of optical openings may also be included.

According to another aspect, the means for retaining may comprise a recessed portion defined by the heated platen configured to surround and retain the slip cover.

In another aspect, a top surface of the slip cover may be substantially flush with a top surface of the heated platen when the slip cover is positioned in the recessed portion of the heated platen.

In yet another aspect, the means for retaining may comprise a frame member configured to retain the slip cover over the at least one of the plurality of optical openings.

According to another aspect, the frame member may be removably attachable to the heated platen.

In one aspect, the frame member may further comprise a recessed portion configured to retain the slip cover in a desired relation to the heated platen.

According to another aspect, the frame member may define a plurality of holes for attaching the frame member to the heated platen.

According to another aspect, the assembly may further comprise a gasket between the slip cover and the heated platen.

In yet another aspect, the gasket may be positioned between an outer edge of the slip cover and the heated platen.

According to another aspect, the assembly may further comprise a gasket positioned between a surface of the slip cover facing the plurality of optical openings and an area of the surface of the heated platen surrounding the plurality of optical openings.

In one aspect, a heated platen assembly for use in a biological testing device is provided comprising a heated platen defining a plurality of optical openings to allow radiation to pass from a first side of the heated platen to a second side of the heated platen, and means for covering at least one of the plurality of optical openings on a side facing away from a sample to be tested. Further, the means for covering at least one of the plurality of optical openings may be transmissive to light.

According to another aspect, retaining means configured to retain the means for covering over at least one of the plurality of optical openings may be provided.

In another aspect, the retaining means may comprise a recessed portion defined by the heated platen.

In yet another aspect, the retaining means may further comprises a frame member configured to retain the slip cover within the recessed portion.

According to another aspect, the retaining means may comprise a frame member configured to retain the slip cover in place over the at least one of the plurality of optical openings.

In yet another aspect, the frame member may include a recessed portion configured to surround and retain the slip cover in place over the at least one of the plurality of optical openings.

In another aspect, a heated platen assembly for use in a biological testing device may be provided comprising a heated platen defining a plurality of optical openings configured to permit radiation to pass from a first side of the heated platen to a second side of the heated platen, a light transmissive slip cover configured to cover at least one of the plurality of optical openings, and a fastening apparatus configured to retain the slip cover over the at least one of the plurality of optical openings.

According to another aspect, the assembly may further comprise a seal member positioned between a surface of the slip cover facing the plurality of optical openings and an area of the surface of the heated platen surrounding the plurality of optical openings.

According to yet another aspect, the fastening apparatus may further comprise a seal member configured to provide a press fit between the slip cover and the heated platen.

According to another aspect, a heated platen assembly for use in a biological testing device may be provided comprising a heated platen defining a plurality of optical openings configured to permit radiation to pass from a first side of the heated platen to a second side of the heated platen, a light transmissive slip cover configured to cover at least one of the plurality of optical openings, and a fastening apparatus configured to retain the slip cover over at least one of the plurality of optical openings. The fastening apparatus may comprise a recessed portion defined by the heated platen configured to surround and retain the slip cover in place over the at least one of the plurality of optical openings, and the fastening apparatus may further comprise a frame member configured to retain the slip cover within the recessed portion.

Other aspects still will become apparent from the description that follows. It should be understood that the invention, in its broadest sense, could be practiced without accomplishing one or more of the aspects described herein.

BRIEF DESCRIPTION OF THE DRAWINGS

The accompanying drawings, which are incorporated in and constitute a part of this specification, illustrate at least one exemplary embodiment.

In the drawings.

DESCRIPTION OF VARIOUS EMBODIMENTS

Figure 1:
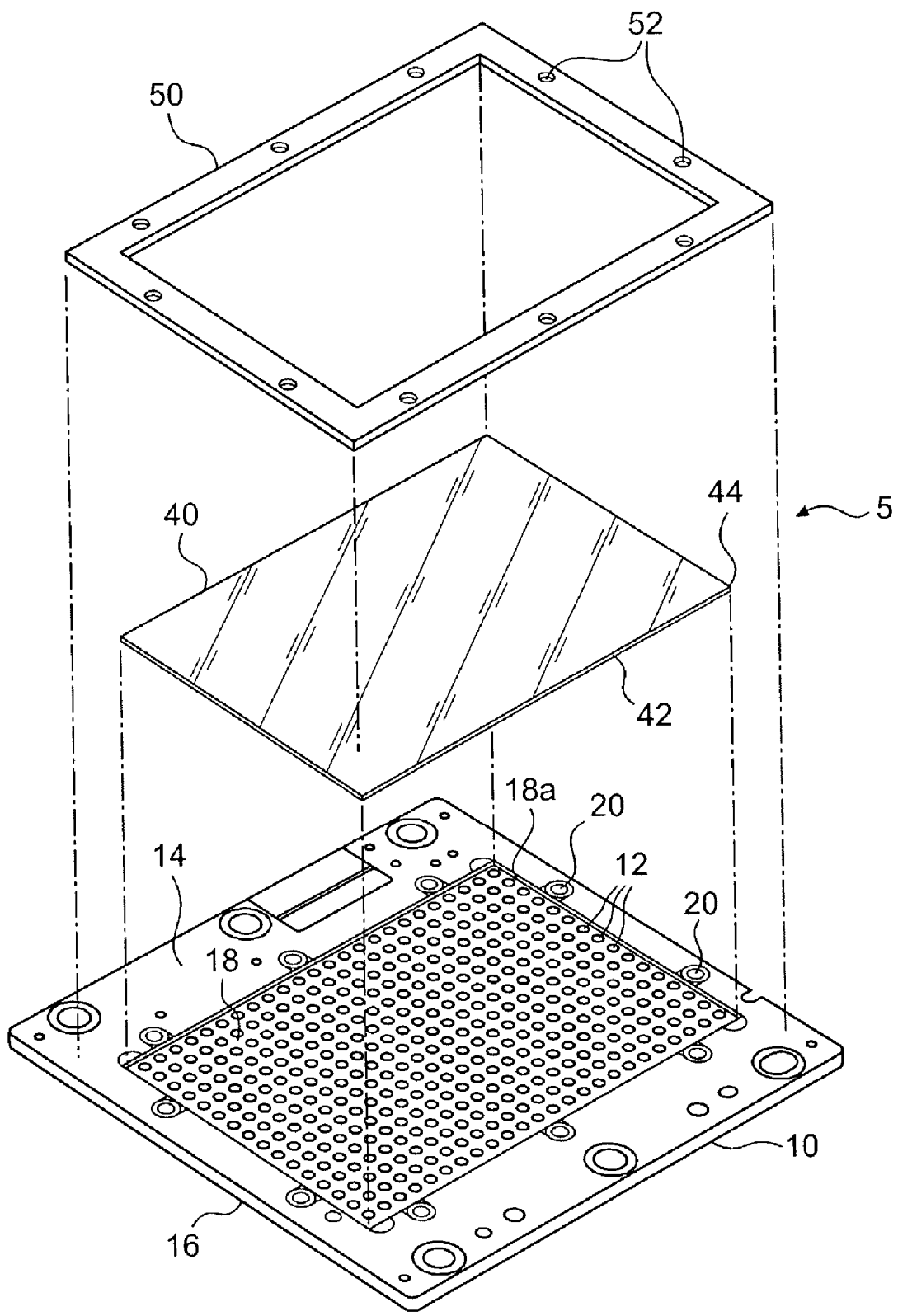
FIG. 1 is an exploded perspective view of a heated platen assembly including a frame for securing a slip cover.

Reference will now be made to non-limiting, exemplary embodiments of the present teachings, examples of which are illustrated in the accompanying drawings. Wherever possible, the same reference numbers are used in the drawings and the description to refer to the same or like parts, and the same reference numbers with alphabetical suffixes or numerical prefixes are used to refer to similar parts.

In accordance with various embodiments, a heated platen assembly is provided. In one aspect, the heated platen assembly may be used in a biological testing device for performing nucleic acid amplification. In various embodiments, the heated platen assembly includes a heated platen, a light transmissive slip cover, and means for retaining the slip cover in a substantially fixed relationship relative to the heated platen. The heated platen assembly may further include additional securing means associated with the slip cover, among other components.

In FIG. 1, an exploded perspective view is shown of a heated platen assembly 5 that includes a heated platen 10 and a slip cover 40. Slip cover 40, as shown, is rectangular in shape and has four edges 42 as well as four corners 44. Slip cover 40 may, however, also be of any suitable shape to fit on a heated platen of choice. Heated platen 10 may be any type of device configured to operate with nucleic acid amplification devices. One common method of performing nucleic acid amplification of biological samples is polymerase chain reaction (PCR). Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674, which are also incorporated herein by reference.

In one embodiment, the thermal cycling device performs real-time detection of the nucleic acid amplification of the samples during thermal cycling.

Real-time detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling. Real-time detection permits accurate and efficient detection and monitoring of the samples during the nucleic acid amplification.

Heated platen 10 may be configured for use with any type of sample well tray, including, for example, 96-well sample well trays, 384-well sample trays, and microcard sample trays. Other configurations include 4, 8, 12, 24, 48, and 1,536 sample wells, among others. The size and shape of these sample well trays are well known in the art. Examples of 96-well sample well trays suitable for use in the present invention are described in WO 00/25922 to Moring et al., the complete disclosure of which is hereby incorporated by reference for any purpose. Examples of sample well trays of the microcard type suitable for use in the present invention are described in WO 01/28684 to Frye et al., the complete disclosure of which is hereby incorporated by reference for any purpose, WO97/36681 to Woudenberg et al., the complete disclosure of which is hereby incorporated by reference for any purpose, U.S. application Ser. No. 09/897,500, filed Jul. 3, 2001, assigned to the assignee of the present invention, the complete disclosure of which is hereby incorporated by reference for any purpose, and U.S. application Ser. No. 09/977,225, filed Oct. 16, 2001, assigned to the assignee of the present application, the complete disclosure of which is hereby incorporated by reference for any purpose. Sample well trays having any number of sample wells and sample well sizes may also be used with the thermal cycling device of the present invention.

The volume of the sample wells may vary anywhere from about 0.01 µl to thousands of microliters (µl), with a volume between 10 to 500 µl being typical.

As embodied herein and shown in FIG. 1, heated platen 10 of the heated platen assembly 5 defines a plurality of optical openings 12. Optical openings 12 pass entirely through heated platen 10 so as to allow optical access from the top surface 14 (see FIG. 4) through to the underside 16 (see FIG. 5). In this fashion, radiation, (e.g. light, such as that emitted from a laser or a light bulb, such as a quartz bulb), may pass through heated platen 10 to a plurality of biological samples located on one side of the heated platen. As depicted in FIGS. 1-5, heated platen 10 defines 384 optical openings 12 to correspond with a sample card or tray having 384 sample wells contained therein. It is common for heated platen 10 to contain a number of optical openings 12 equal to a number of sample wells contained in the card or tray being used for testing, but the heated platen could instead have a number of openings different than the number of sample wells, if desired.

In certain embodiments, heated platen 10 also includes a recessed area 18 substantially surrounding the plurality of optical openings 12 for receiving slip cover 40. As depicted in FIG. 1, recessed area 18 is of a depth approximately equal to a thickness of slip cover 40 so as to allow slip cover 40 to be flush with the portion of heated platen 10 surrounding recessed area 18 when slip cover 40 is positioned in recessed area 18 of heated platen 10. Recessed area 18 may instead, however, be of a depth greater than or less than a thickness of slip cover 40. Recessed area 18 defines a substantially flat surface for contacting a surface of the slip cover facing optical openings 12. Although heated platen 10, slip cover 40 and recessed area 18 are depicted as being rectangular in shape, these components may be of any shape suitable for operating in conjunction with a sample well tray.

Also depicted in FIG. 1 is frame member 50 used as a fastening apparatus to hold slip cover 40 in place. As used herein, the fastening apparatus may include, but is not limited to a frame member, a recessed area, a gasket, an adhesive, or a clip device or devices positioned on heated platen 10. Other FINNEGAN fastening apparatus known in the art are also contemplated that can perform the function of retaining slip cover 40, or other covering apparatus in place over at least one of the plurality of optical openings 12. Frame member 50 may be made of any suitable material, for example sheet metal or any other material suitable for withstanding operating temperatures of approximately 80° C. or higher. In addition, other temperature ranges suitable for biological or other testing using a heated platen may be desirable and it is contemplated that a material for frame member 50 would be appropriately suited for the desired temperature range.

Figure 2:
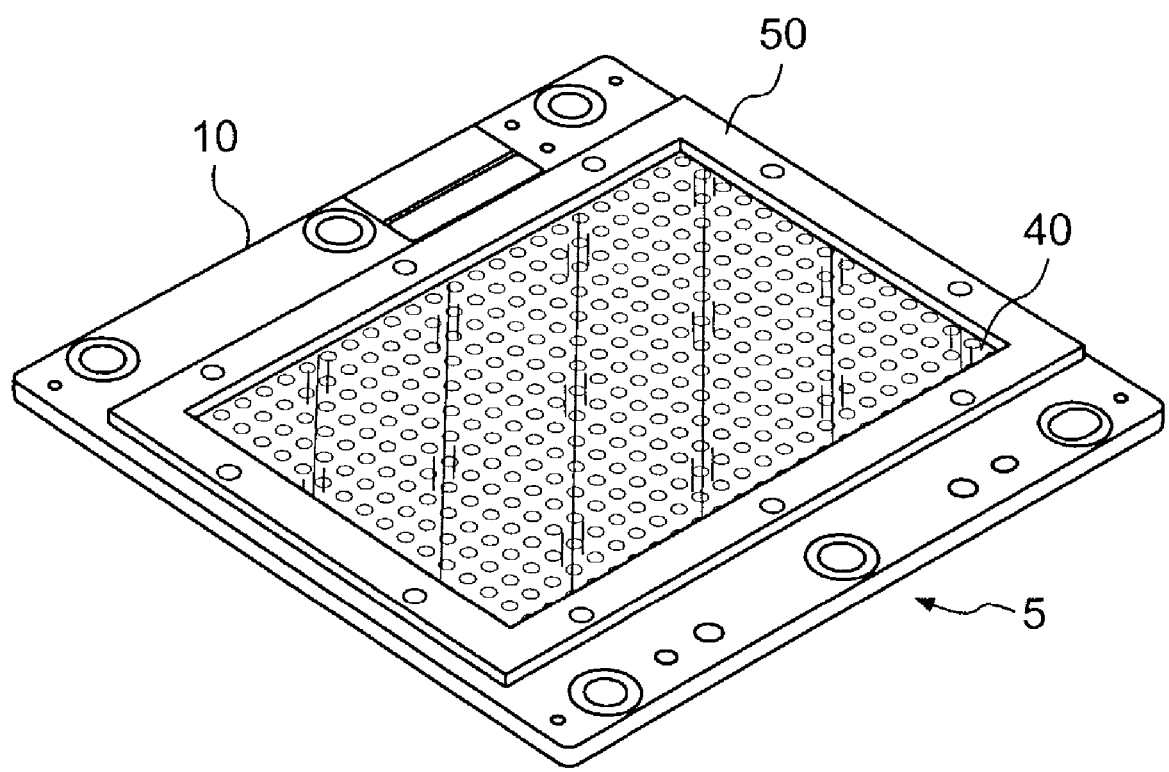
FIG. 2 is a perspective view of the assembled heated platen assembly of FIG. 1.
Figure 6:
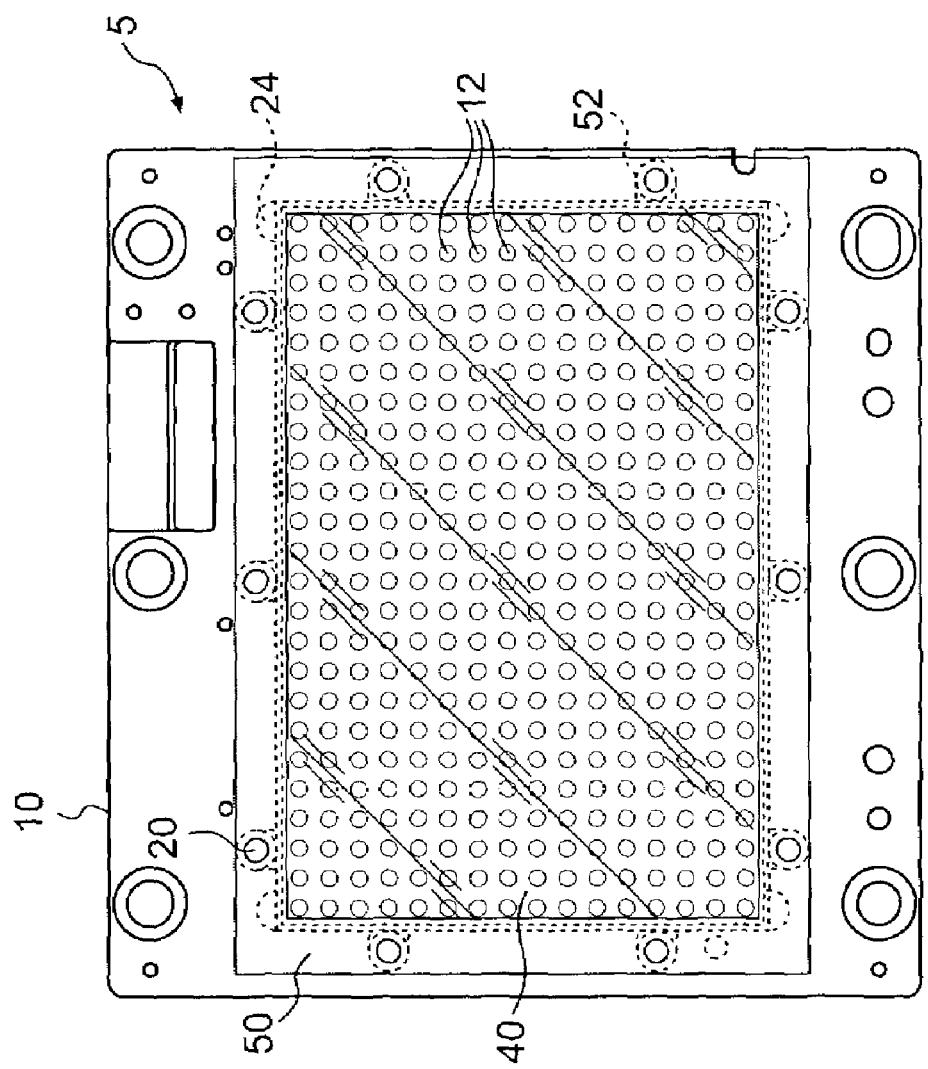
FIG. 6 is a plan view of the assembly depicted in FIG. 2.

In the embodiment shown in FIGS. 1-5, frame member 50 is configured to assist in holding slip cover 40 in a substantially stationary position relative to heated platen 10. As seen in FIG. 2, frame member 50 and slip cover 40 are in place on heated platen 10. Frame member 50 defines a plurality of holes 52 that correspond to a plurality of holes 20 located in platen 10 (see FIG. 1). A fastening device (not shown), for example a screw or any other suitable device, may then be inserted through hole 52 into hole 20 to hold frame member 50 in place. An outer periphery of slip cover 40 is thereby sandwiched between frame member 50 and recess 18 of heated platen 10. Frame member 50 may be dimensioned so that it does not obscure any of optical openings 12 when it is in place on heated platen 10. In the example shown in FIG. 6, frame member 50 overlaps slip cover 40 by a small amount, for example 0.3 mm. This overlap may be varied from small to quite large.

Figure 3:
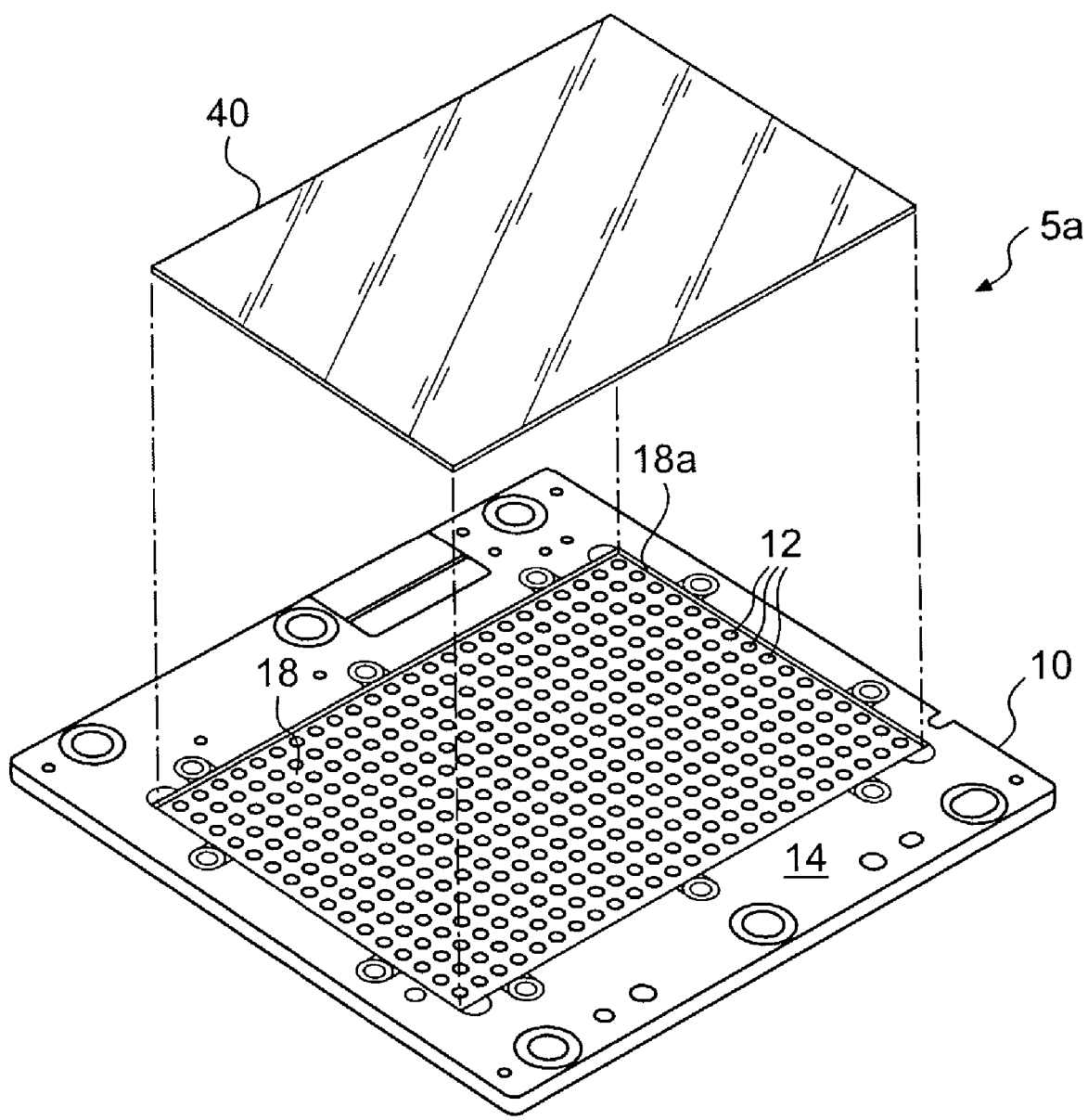
FIG. 3 is an exploded perspective view of another embodiment of a heated platen assembly including a slip cover.
Figure 3A:
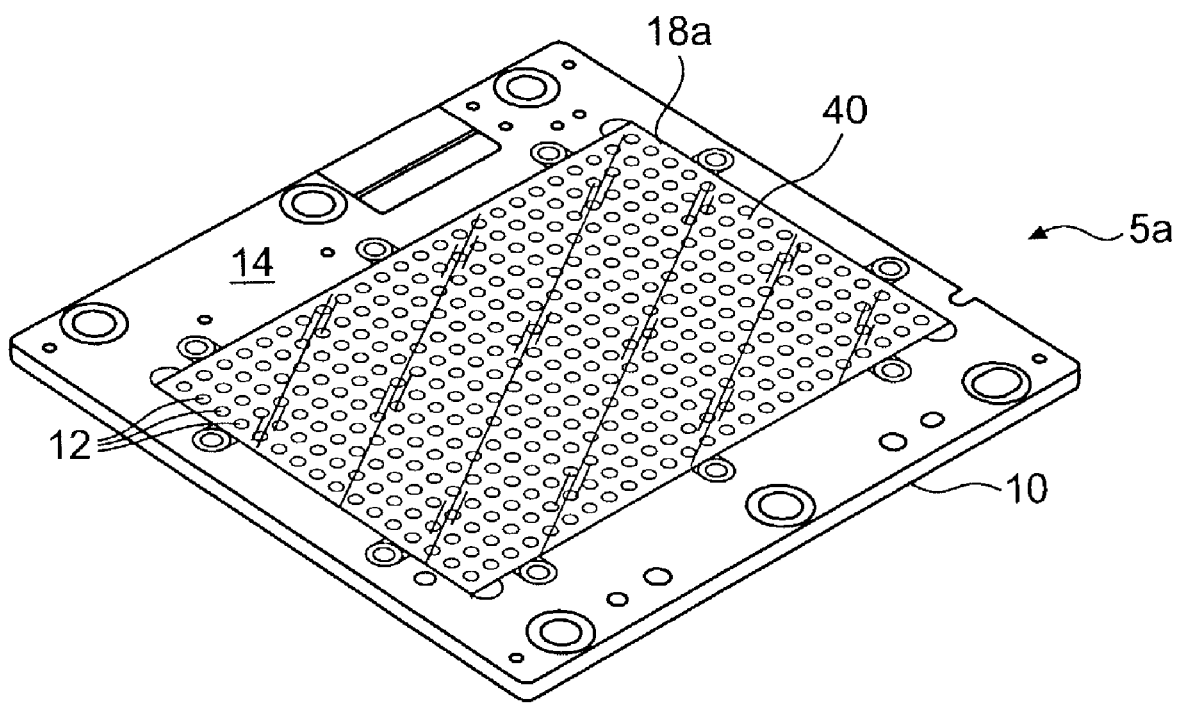
FIG. 3a is a perspective view of the assembled heated platen assembly of FIG. 1.

Other variations also exist for maintaining slip cover 40 in place on heated platen 10. In the embodiment depicted in FIGS. 3 and 3a, it is possible that recess 18 alone may be sufficient to hold slip cover 40 in place simply by utilizing a border or wall portion 18a of recess 18 to confine/surround and restrict movement of slip cover 40. In such an embodiment, frame member 50 could be omitted and recessed area 18 could be sufficient, along with gravity, to keep slip cover 40 in a desired position relative to heated platen 10.

In addition to providing essentially a drop-in configuration whereby gravity holds slip cover 40 in place, it may also be desirable to place a gasket (not shown) or other suitable device around the perimeter of recessed area 18 to allow for a press fit of the slip cover. Such a press fit could retain slip cover 40 regardless of orientation. It may also be possible to utilize tight tolerance manufacturing to provide such a press fit without the use of any additional gasket or other device whereby slip cover 40 may be retained in recessed portion 18 through a contact fit between heated platen 10 and slip cover 40 alone.

In certain embodiments, an adhesive or other suitable material is utilized to fasten slip cover 40 permanently or semi-permanently in place onto heated platen 10. This adhesive may be applied around the perimeter of recess 18 and/or on the area of recess 18 between the plurality of holes 12.

Frame member 50 may also be provided with a recessed portion configured to accommodate slip cover 40. If slip cover 40 is of a thickness greater than recess 18, then the recessed portion of frame member 50 may be used to assist in holding slip cover 40 in place. In addition, it is contemplated that heated platen 10 may not have a recessed portion 18, in which case the recessed portion of frame member 50 may be utilized to restrict movement of the slip cover. In either of these embodiments, frame member 50 and slip cover 40 may be fixed together to form a single frame member/slip cover assembly that may then be affixed to the heated platen 10 as described herein or by any other means suitable for affixing to the heated platen 10.

Figure 4:
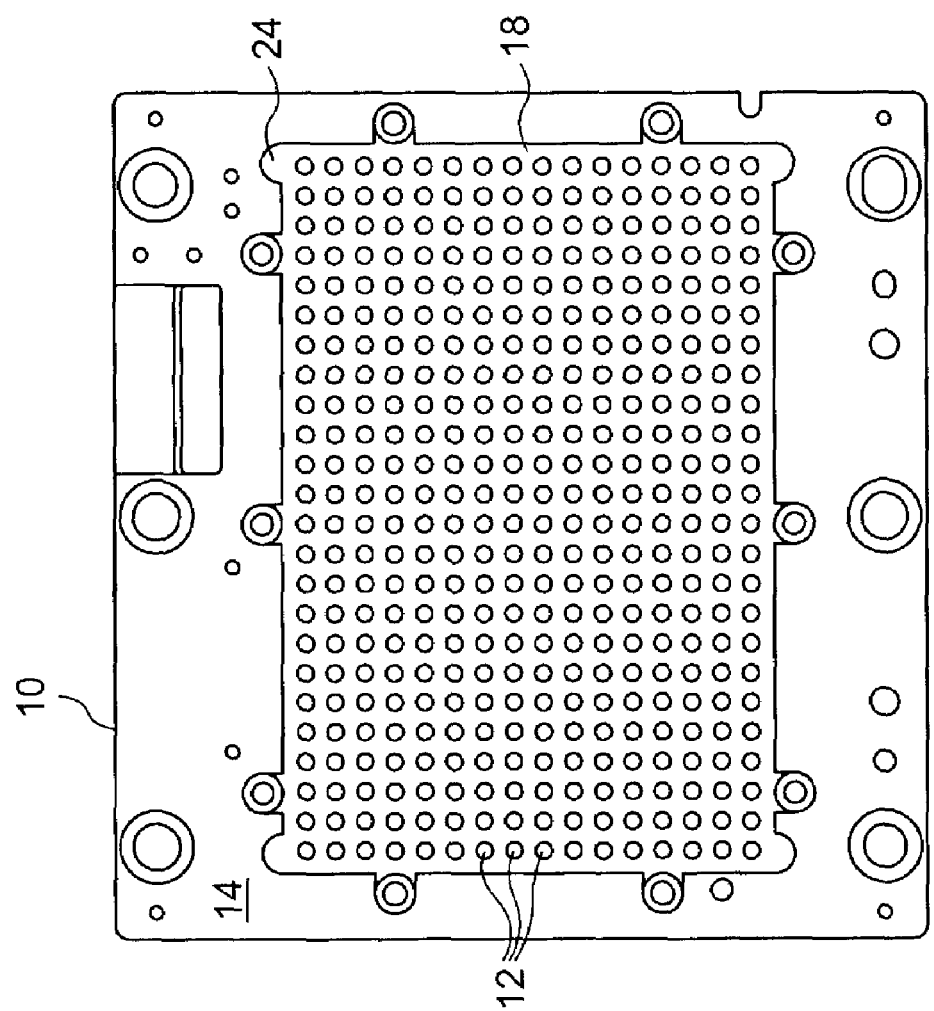
FIG. 4 is a plan view of a top side of the heated platen assembly of FIG. 1.
Figure 5:
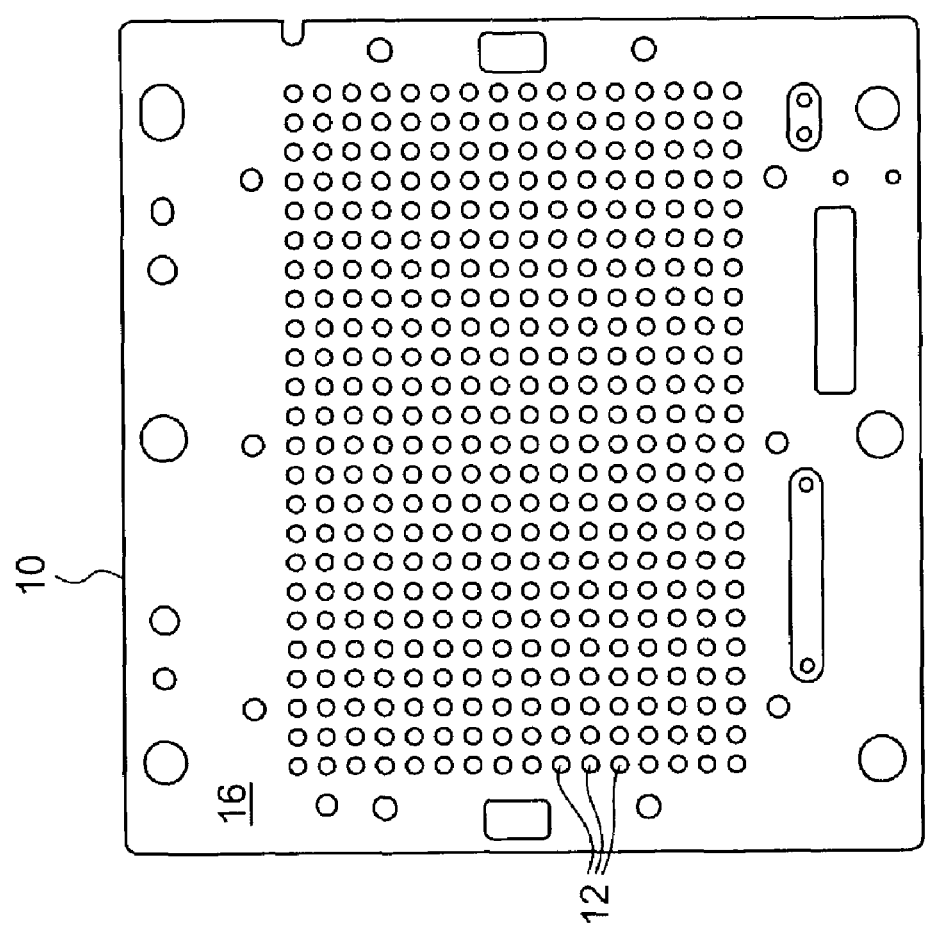
FIG. 5 is a plan view of an underside of the heated platen assembly of FIG. 1.

FIG. 4 depicts a plan view of heated platen 10 looking down onto top surface 14. As can be seen in FIG. 4, heated platen 10 may include one or more relief areas 24 around the perimeter of recess 18. Relief areas 24 may be provided to allow easier access to an edge 42 or corner 44 of slip cover 40 so that slip cover 40 may be more easily removed from recessed area 18. Although relief areas 24 are depicted as semicircular in shape, these relief areas may be of any shape suitable for allowing access to edge 42 or corner 44 of slip cover 40.

Slip cover 40 may be made of any suitable material that will allow for the transmission of radiation, such as light, through to optical openings 12 and into the biological samples (not depicted). For example, slip cover 40 may be made of glass or plastic. Slip cover 40 may also be made of a light transmissive film material that may be cut to a proper size to fit over the optical openings as desired. Because vertical or "head" space in PCR devices is often limited, it may be desirable to have a slip cover of a relatively small thickness. In certain embodiments, the slip cover thickness may be in the range of 0.5 mm or less. In such an instance, recess 18 may be deep enough to allow slip cover 40 to rest entirely below upper surface 14 of heated platen 10 or be flush with surface 14.

It may also, however, be desirable to utilize a thicker slip cover that may allow for rounding, chamfering, or otherwise blunting of any potentially sharp edges of slip cover 40. In addition, a thicker slip cover may be more durable than a thinner one.

Other suitable materials for slip cover 40 include clear, non-fluorescing polycarbonates, such as LEXAN. It may be desirable to provide a slightly thicker cover if it is made out of a polycarbonate or other similar material because of its tendency to fluoresce at low thicknesses. For example, it may be desirable to have a LEXAN slip cover with a thickness in the range of approximately 0.6 to 3.2 mm. Other materials may also be contemplated for use as slip cover 40 that are capable of withstanding the operating temperatures achieved with the heated platen.

To further enhance the dust accumulation prevention of slip cover 40, a gasket or other type of seal member (not shown) may be provided between heated platen 10 and slip cover 40. Such a gasket may be similar to the gasket described above where it may be situated around the edges 42 of slip cover 40 for providing a press-fit or the gasket may be provided sandwiched between the surface of slip cover 40 facing toward optical openings 12 and the surface of heated platen 10 in the area surrounding the matrix of optical openings 12. This gasket, or o-ring, may be made of any suitable material used for such gaskets. The seal could also include a heat resistant material suitable for the operating temperature range of the heated platen that could be applied in viscous form around the perimeter of the plurality of openings, which would harden into a seal that would then be affixed to heated platen 10. The seal/gasket could be made, for example, from Neoprene, Buma-N, Viton, Teflon, Kalrez, silicone or other similar material suitable for use in a PCR environment. This seal could also be applied in the alternative to slip cover 40. This gasket or seal member located between heated platen 10 and slip cover 40 may thus provide an additional barrier to foreign matter that may clog optical openings 12. This barrier may also be provided as a substantially air-tight seal.

As mentioned above, heat loss through the optical openings in the heated platen can be a problem with conventional devices. As an additional advantage, a slip cover as described herein may also reduce the warm-up time required to raise the heated platen temperature from ambient to a desired operating temperature. In one non-limiting example, the slip cover described herein may reduce warm-up time to an operating temperature of 103° C. by, for example, nearly 50%.

Figure 7:
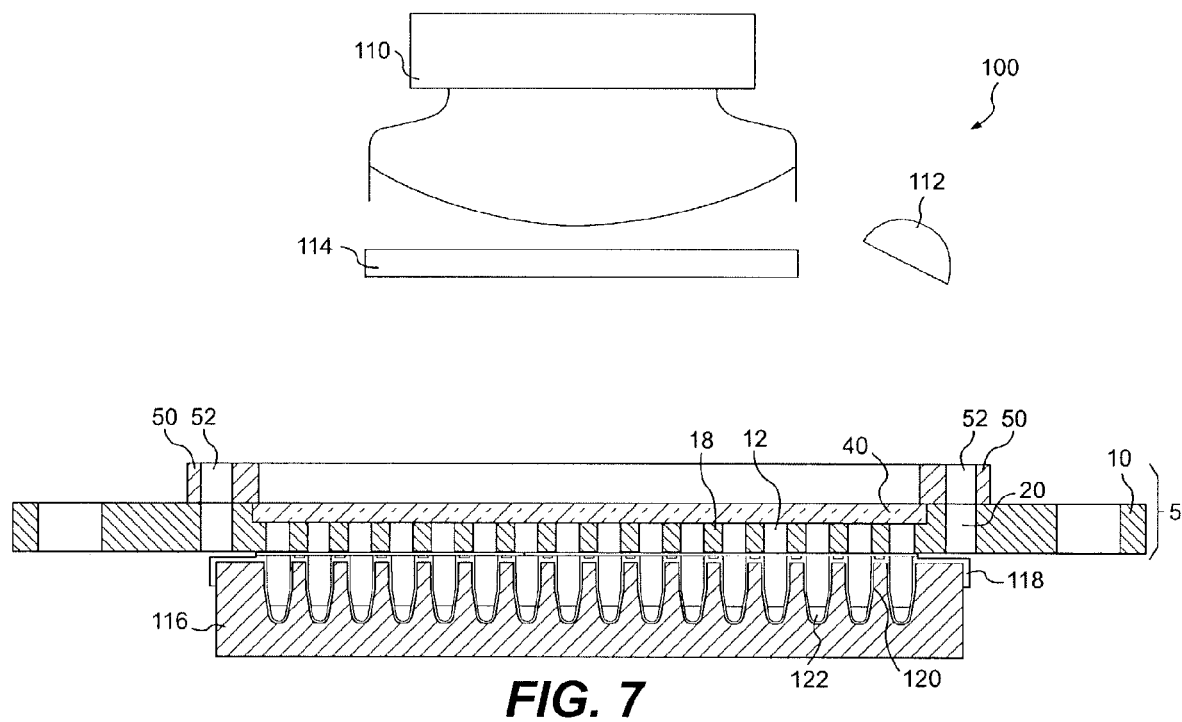
FIG. 7 is a partial section view of the heated platen of FIG. 1 in conjunction with an exemplary biological testing device.

As depicted in FIG. 7, heated platen assembly 5 is depicted in place in an exemplary embodiment of a biological testing device 100. Testing device 100, in this exemplary embodiment, includes a optical detection device 110, for example a CCD camera, a light source 112, a lens 114, heated platen assembly 5, sample block 116, and sample well tray 118. Sample well tray 118 comprises a plurality of sample wells 120 for containing samples 122. In operation, light emitted from light source 112 interacts with the samples 122. Light emitted and/or reflected from samples 122 then travels through optical openings 12 and passes through slip cover 40. The light may then be focused and or collimated, for example, by lens 114 before being received by detection device 110. Further examples of biological testing apparatus usable in conjunction with heated platen 5 are described in one or more of the documents incorporated by reference herein. Heated platen 5 may also be suitable for other testing devices than the one depicted in FIG. 7.

It is intended that the specification and examples be considered as exemplary only.

What is claimed is:

1. A biological testing device for samples, comprising:
   a heated platen assembly, the assembly comprising:
   a heated platen defining a plurality of optical openings, the optical openings configured to permit radiation to pass through the heated platen, the heated platen having a first side configured to face away from a plurality of sample wells and a second side configured to face toward the plurality of sample wells, wherein the heated platen is connected to a resistive element;
   a light transmissive slip cover configured to cover at least one of the plurality of optical openings on the first side of the heated platen; and
   a frame member over the plurality of optical openings, wherein the frame member overlaps with the slip cover and does not obscure any of the optical openings, and wherein the frame member is attached to the heated platen via holes in the frame member and the heated platen;
   wherein the heated platen comprises a recessed portion surrounding and retaining the cover slip and the slip cover is adhered to the heated platen; and
   an optical detection device, the optical detection device comprising a real-time detector of nucleic acid amplification in the samples during thermal cycling; and
   a light source, wherein both the radiation passing from the light source to the sample wells and from the sample wells to the optical detection device pass through the same optical opening.

2. The heated platen assembly of claim 1, wherein a top surface of the slip cover is substantially flush with a top surface of the heated platen when the slip cover is positioned in the recessed portion of the heated platen.

3. The heated platen assembly of claim 1, wherein the frame member further comprises a recessed portion configured to retain the slip cover in a desired relation to the heated platen.

4. The heated platen assembly of claim 1, wherein the frame member comprises sheet metal.

5. The heated platen assembly of claim 1, wherein the slip cover comprises glass.

6. The heated platen assembly of claim 5, wherein the slip cover has a thickness of approximately 0.5 mm or less.

7. The heated platen assembly of claim 1, wherein the slip cover comprises a non-fluorescing clear polycarbonate.

8. The heated platen assembly of claim 7, wherein the slip cover has a thickness of approximately 0.6 mm to approximately 3.2 mm.

9. The heated platen assembly of claim 1, further comprising a gasket between the slip cover and the heated platen.

10. The heated platen assembly of claim 9, wherein the gasket is positioned between an outer edge of the slip cover and the heated platen.

11. The heated platen assembly of claim 9, further comprising a gasket positioned between a surface of the slip cover facing the plurality of optical openings and an area of the surface of the heated platen surrounding the plurality of optical openings.

12. The heated platen assembly of claim 1, wherein the heated platen defines 4, 8, 12, 24, 48, 96, 384, or 1,536 optical openings.

13. A biological testing device for samples, comprising:
   a heated platen assembly, the assembly comprising:
   a heated platen defining a plurality of optical openings, the optical openings configured to permit radiation to pass through the heated platen, the heated platen having a first side configured to face away from a plurality of sample wells and a second side configured to face toward the plurality of sample wells, wherein the heated platen is connected to a resistive element;
   a light transmissive slip cover configured to cover at least one of the plurality of optical openings on the first side of the heated platen; and
   a frame member over the plurality of optical openings, wherein the frame member overlaps with the slip cover and does not obscure any of the optical openings, and wherein the frame member is attached to the heated platen via holes in the frame member and the heated platen,
   wherein the slip cover is adhered to the heated platen; and
   an optical detection device, the optical detection device comprising a real-time detector of nucleic acid amplification in the samples during thermal cycling; and
   a light source, wherein both the radiation passing from the light source to the sample wells and from the sample wells to the optical detection device pass through the same optical opening.

14. The testing device of claim 13, wherein the heated platen comprises a recessed portion.

* * * * *